(12) United States Patent
Pernot

(10) Patent No.: US 8,075,311 B2
(45) Date of Patent: Dec. 13, 2011

(54) REMOVABLY FIXING A DENTAL INSTRUMENT WITH A RETRACTABLE CATCH RELATIVE TO A DRIVE SHAFT AXIS

(75) Inventor: Jacques Pernot, Vieilley (FR)

(73) Assignee: Micro Mega International Manufactures (Societe Anonyme), Besancon (FR)

( * ) Notice: Subject to any disclaimer, the term of this patent is extended or adjusted under 35 U.S.C. 154(b) by 775 days.

(21) Appl. No.: 11/910,904

(22) PCT Filed: Feb. 24, 2006

(86) PCT No.: PCT/FR2006/000418
§ 371 (c)(1),
(2), (4) Date: Oct. 5, 2007

(87) PCT Pub. No.: WO2006/128982
PCT Pub. Date: Dec. 7, 2006

(65) Prior Publication Data
US 2008/0182226 A1 Jul. 31, 2008

(30) Foreign Application Priority Data
Jun. 3, 2005 (FR) .................................. 05 05609

(51) Int. Cl.
*A61C 1/14* (2006.01)

(52) U.S. Cl. ............................. 433/128; 279/75; 279/82
(58) Field of Classification Search ................... 433/126, 433/127, 128; 279/43, 50, 57, 75, 82
See application file for complete search history.

(56) References Cited

U.S. PATENT DOCUMENTS 5,037,299 A * 8/1991 Nakanishi ...................... 433/128
5,704,786 A * 1/1998 Quinn ............................. 433/128

FOREIGN PATENT DOCUMENTS

DE 2918816 12/1979
DE 10311455 9/2004
EP 0470324 2/1992

* cited by examiner

*Primary Examiner* — Cris L Rodriguez
*Assistant Examiner* — Eric Rosen
(74) *Attorney, Agent, or Firm* — Egbert Law Offices PLLC

(57) ABSTRACT

A head assembly for attaching to a dental instrument has a body, a rotary shaft with a pinion thereon, at least one retractable catch latching lever and a retractable catch. The rotary shaft has a central bore suitable for receiving a shank of the dental instrument therein. The latching lever has a peg engageable with an annular latching groove of the shank of the dental instrument. The catch has a positioning plane coinciding with the drive flat of the instrument. The body has a circular opening closed off by a push button cooperative with the rotary shaft so as to release the shank of the dental instrument.

9 Claims, 3 Drawing Sheets

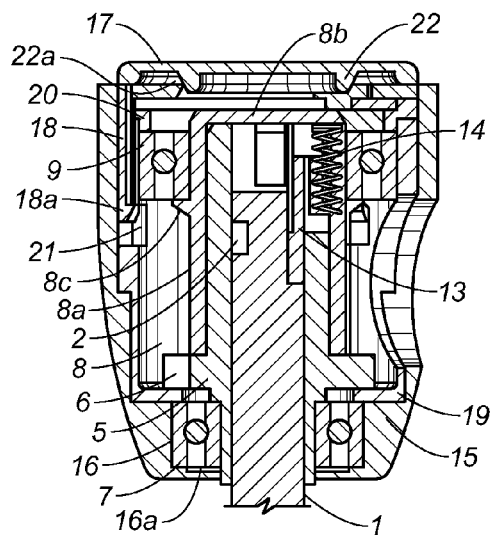
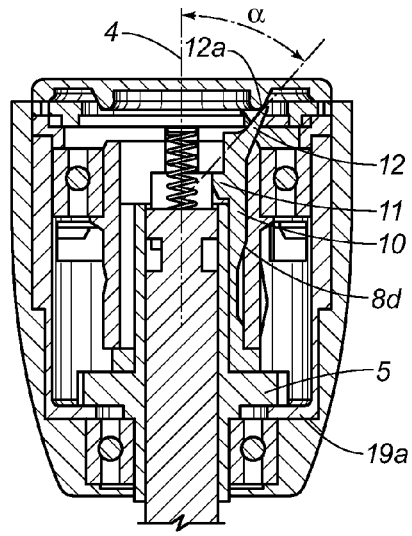
FIG. 2
FIG. 3
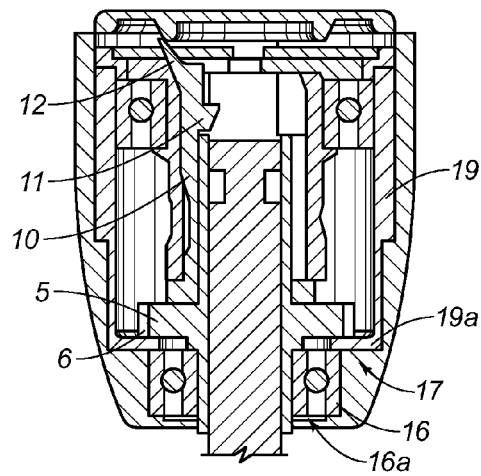
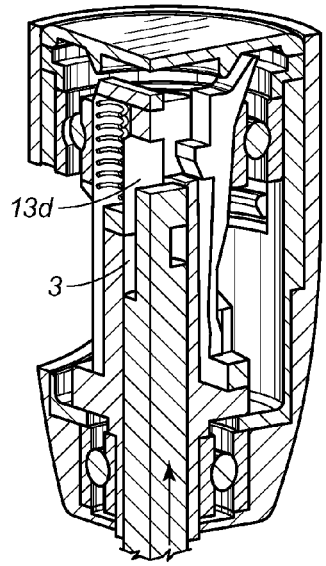
FIG. 4
FIG. 13
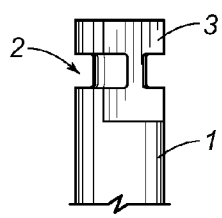
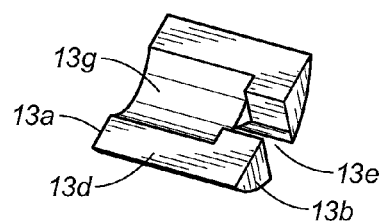
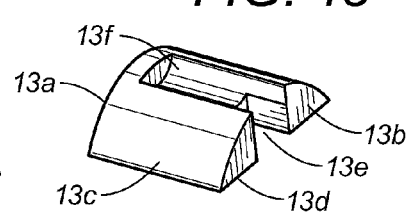
FIG. 1
FIG. 11
FIG. 12

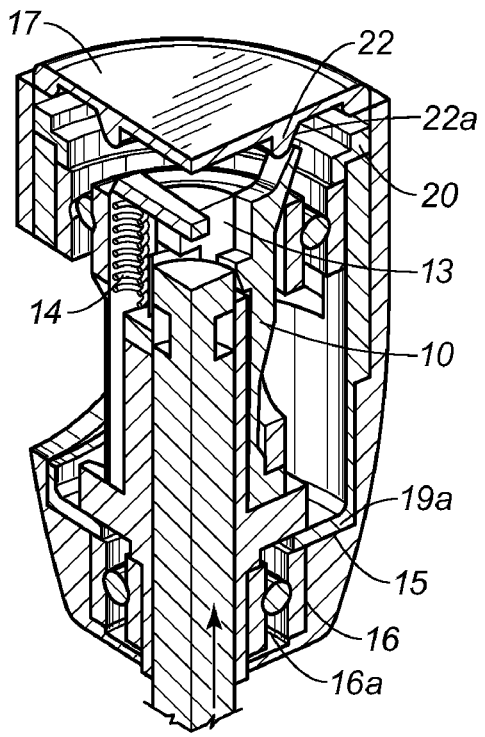
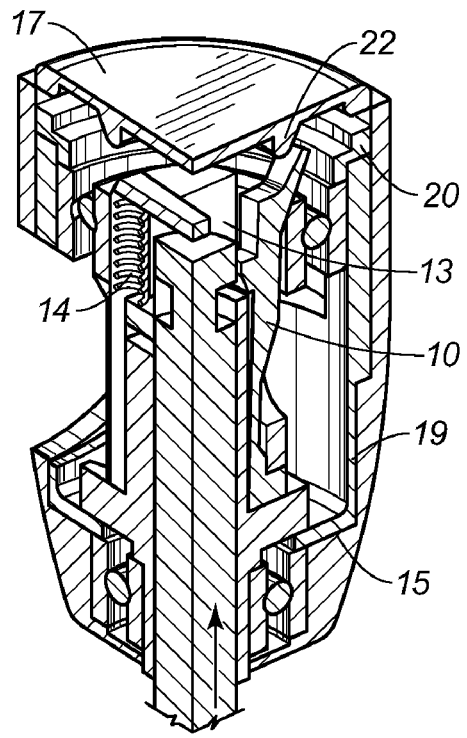
FIG. 7    FIG. 8
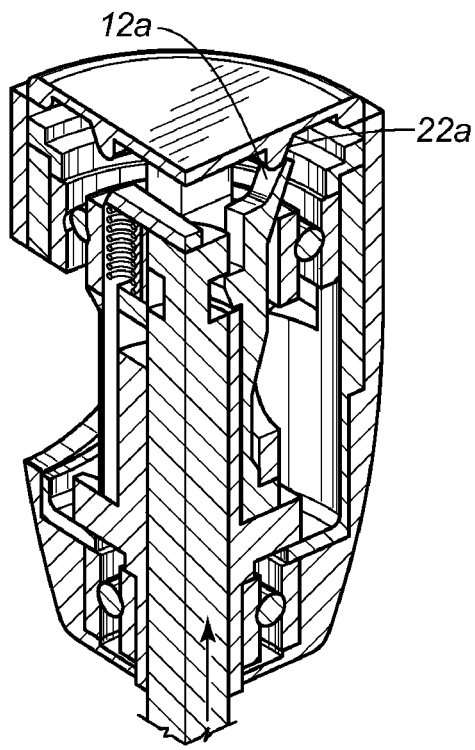
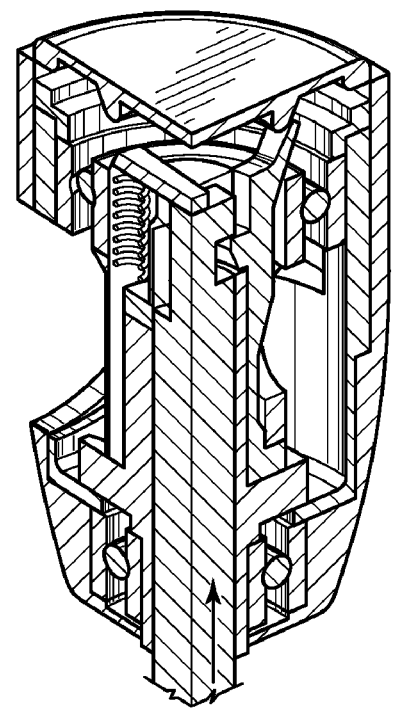
FIG. 9    FIG. 10

REMOVABLY FIXING A DENTAL INSTRUMENT WITH A RETRACTABLE CATCH RELATIVE TO A DRIVE SHAFT AXIS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a new way of removably fixing a dental instrument into the head of a handpiece.

2. Description of Related Art Including Information Disclosed Under 37 CFR 1.97 and 37 CFR 1.98.

Dental instruments, dental burs or endodontic instruments, for example, are generally made up of an active part and a shank (see FIG. 1) for fixing them into handpieces, of the right-angle handpiece type or contra-angle handpiece type.

There is a standard defining the shank for instruments used at low speed. According to this standard, the shank of the instruments is cylindrical and has a groove (a) for axially retaining them and a flat (b) for rotationally driving them.

Numerous fixing devices for these instruments have been described. They force the user to find the angular position of the instrument such that the flat can engage in the combined shape of the latching device while at the same time operating a push-button system able to open the latching device, which collaborates with the groove of the shank of the instrument.

Devices such as the one described in French patent FR 2 555 041 make it possible to dispense with the need to operate a push-button, but there is still a need to find the correct angular position of the instrument in order to engage the flat.

These operations force the user to pick up the instrument in his or her hand, even though this instrument has been sterilized and is generally placed on a stand. Now, the search for the best possible conditions of asepsis during interventions demands that these sterilized instruments must not be touched before they are used.

The chief objective of the invention is to alleviate the aforementioned disadvantages.

BRIEF SUMMARY OF THE INVENTION

The invention achieves this objective by proposing a latching device for attaching a dental instrument into a head of a handpiece of the right angle handpiece type or contra-angle handpiece type. The latching device comprises members for transmitting rotational movement to the instrument, these including a rotary shaft equipped with a pinion so that its rotation can be driven from a driving pinion. The shaft is mounted in the conventional way in a lower bearing or rolling bearing and comprises a central bore intended to accept the shank of a dental instrument. The shank is made up of a cylindrical body provided with an annular latching groove for axial retention of the instrument, and a drive flat, parallel to the longitudinal axis of the instrument and intended to prevent it from turning by collaborating with a flat belonging to the shaft. The head comprises a circular upper opening for mounting members of said transmission, this opening being closed off by a push-button, actuation of which releases the instrument.

The invention includes, in combination:
at least one retractable latching lever comprising a peg to fit into the annular groove; and
a retractable catch that rotates as one with the rotary shaft and comprises a positioning plane to coincide with the flat of the instrument.

The catch can be retracted longitudinally or radially with respect to the axis of the shaft.

More specifically, the invention relates to a device for attaching instruments comprising a rotary shaft intended to accept the instrument and rotationally drive it. The device for attaching comprises, on the one hand, a device that has at least one peg that can be retracted elastically at right angles to the axis of the housing for the instrument until it can fit into the latching groove thus axially retaining the instrument and, on the other hand, a catch that rotates as one with the rotary shaft and which, in combination with the rotary shaft, gives the shape combined with that of the driving flat of the shank of the instrument which has the particular feature of retracting radially or longitudinally if the flat is correctly orientated and resumes the position in which it rotationally drives the instrument. The flat of the instrument generally adopts the appropriate position when turned as soon as the slightest rotational force is applied to it. The instrument is released by action on a push-button for example, which moves the peg aside or radially retracts it.

BRIEF DESCRIPTION OF THE SEVERAL VIEWS OF THE DRAWINGS

The invention will be better understood with the aid of the description given hereinafter with reference to the following attached figures.

FIG. 1 depict a schematic view of a shank of a dental instrument of the standardized type.

FIGS. 2, 3, and 4 are axial sectional views of a head of a handpiece equipped with a latching device according to one non-limiting embodiment of the invention.

FIGS. 5 to 10 are partial three-dimensional sectional views of the embodiment shown in FIGS. 2 to 4, showing the insertion and latching of an instrument which has been offered up in any arbitrary angular position.

FIGS. 11 and 12 show perspective views of a retractable catch according to the invention.

FIG. 13 is a partial three-dimensional sectional view of the same embodiment as in FIGS. 5 to 10, showing the insertion and latching of an instrument which has been offered up in an angular position that causes its flat to coincide directly with a corresponding shape of the head.

DETAILED DESCRIPTION OF THE INVENTION

Figure 5:
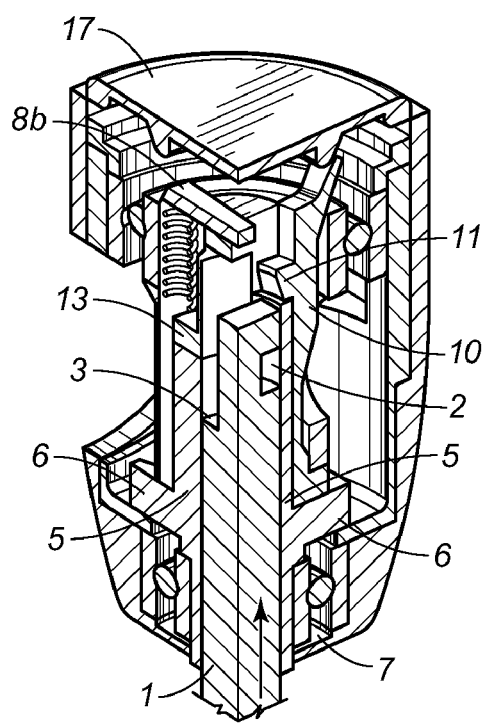

Reference is made first of all to FIGS. 2 to 4 which show a contra-angle head according to the invention, in which a shank of a standardized dental instrument like that of FIG. 1 is held.

The figures show the rear part of the shank of a dental instrument, the shank being made up of a cylindrical body (1) that has a latching groove (2) and a driving flat (3).

In the head of the contra-angle handpiece, there is a rotary shaft (5) equipped with a pinion (6) so that its rotation can be driven from a driving pinion that has not been depicted. The shaft (5) is mounted in the conventional way in a lower bearing or rolling bearing (7). The shaft (5) is covered by a cap (8) which rotates and translates as one therewith, said cap being positioned in an upper bearing or rolling bearing (9).

The cap (8) is made up of a cylindrical envelope (8a) mounted coaxial with the longitudinal axis (4) of the shaft, and of a bridge (8b) secured to the envelope, and positioned diametrically on the top of the cap.

The envelope (8a) of the cap is provided with an external peripheral stop (8c) the purpose of which will be detailed later on.

The envelope also comprises two slits (8d) positioned parallel to the axis (4) and diametrically opposed, and which extend over the entire length of the envelope.

One function of said cap (8) is to hold and fix against the shaft one or more, for example, two, elastic latching levers (10) each of which runs parallel to the longitudinal axis (4) of the shaft.

The bottom end of a lever presses against the upper surface of the pinion (6) while the top end is extended by an inclined point (12) diverging away from the axis (4) at an angle ( ) with respect to the axis (4) so that internally it has an inclined plane (12a), the function of which will be detailed later on.

Each lever also comprises a peg (11) projecting toward the axis (4) and dimensioned such that it can fit into the groove (2) of the instrument.

The slits (8d) of the cap are dimensioned such that the levers (10) can deform and engage in the slits in order to keep the pegs radially apart.

A catch (13) resting on the shaft pinion is held captive inside the cap and can slide inside the latter. These constraints define the shape of the catch, which is visible in FIGS. 11 and 12, delimited by a lower plane (13a) that rests upon the upper surface of the shaft, an upper plane (13b), that can come into abutment with the underside of the bridge, a cylindrical outer envelope (13c) with the same concavity as the inside of the envelope of the cap, and a lateral plane (13d) perpendicular to the lower plane and to the upper plane.

On its top, the catch has a slit (13e) or slot, positioned radially and transversely, and on its lateral wall it has a longitudinal cylindrical groove (13f) emerging laterally, and, on the top of the catch, and extending over just part of the length thereof, so as to act as a housing for a compression spring (14) held captive between the bottom of the groove (13f) on the one hand, and the underside of the bridge (8b) of the cap on the other hand.

The catch also has a cylindrical internal bore 13g of substantially the same radius, give or take operating clearances, as the body of an instrument, so as to be able to slide externally relative to said instrument body.

Engaging the slit (13e) with the bridge (8b) of the cap provides rotational drive of the catch and also allows it to slide under the action of an axial force, directed toward the bridge (8b) and exerted by an object introduced into the central and axial bore of the rotary shaft (5) and intended to accept the instrument.

To make it easier to fit the latching device in the head of the handpiece, all the elements of said latching device are mounted in a sleeve (19) of a substantially cylindrical shape having, at the bottom end, a circular transverse rim (19a), directed toward the axis (4), see FIG. 2 et seq.

Once the lower bearing (7) has been positioned in its housing (16), the sleeve (19) comprising all the elements already mounted inside it is introduced from the top of the head until it comes into axial abutment at the bottom on an inner shoulder (15) of the head.

The lower bearing (7) is thus halted axially downward by the bottom (16a) of its housing and, upward, by the transverse rim (19a) of the sleeve, which projects with respect to the shoulder (15) of the head.

The lever or levers (10) is or are positioned against the shaft of the pinion, in abutment with said pinion, and facing the slits (13e) of the cap. Each lever is immobilized at the bottom by the enclosure of a return (10a) in the sleeve (19) so as to allow their top parts to spring back once they have been parted.

The upper bearing is immobilized axially downward by the peripheral stop (8c) of the cap, and upward by an annular stop (20) engaged in the upper opening of the sleeve.

Said annular stop (20) is provided with at least two slits (20a) parallel to the axis (4) and designed to allow the passage of latching arms (18) secured to a push-button (17) closing off the opening in the head of the handpiece.

Each latching arm (18) is provided at its end with a hook (18a) directed toward the axis (4) and intended to engage in a cutout (21) or a complementary shape made in the sleeve.

The push-button also comprises, on its underside, an annular shape (22) with a tapering outer wall, facing toward the cap.

The diameter of this annular shape (22) is designed such that its tapering outer wall (22a) engages with the inclined plane (12a) of each point (12) of the elastic levers (10), when the push-button is depressed, thus causing the levers (10) to disengage and part and disengaging the pegs (13).

The way in which the device according to the invention works will now be described.

The operator, having picked up the handpiece, offers the head of said handpiece to the selected instrument and inserts this instrument into the shaft (5) without having to concern himself with the position of the flat belonging to the instrument.

In the case of FIGS. 6 to 10, the flat of the instrument is in some arbitrary angular position with respect to the catch (13).

Figure 6:
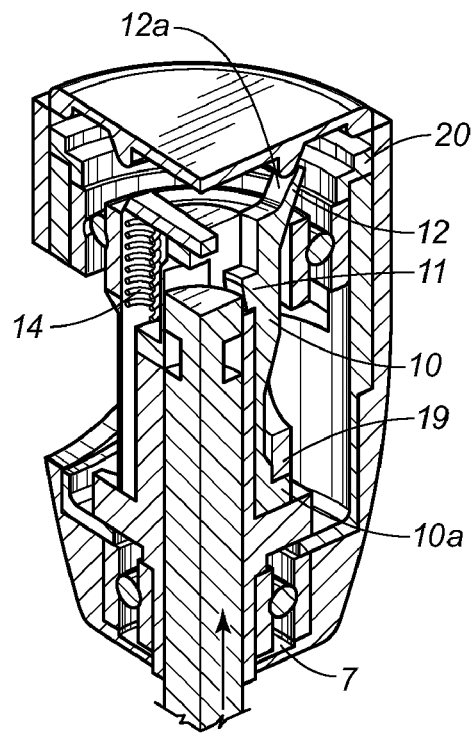
Figure 14:
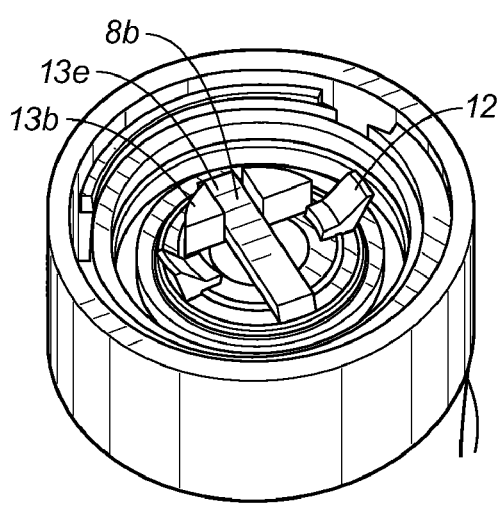
FIGS. 14 and 15 are partial upper perspective views corresponding to FIGS. 9 and 10.

The body slides upward relative to the head until it comes into abutment with the pegs (11) of the levers (10) and radially parts them (FIG. 6). Said levers begin to part. Insertion of the instrument continues (FIGS. 7 and 8) with the levers parting radially (FIG. 8) when the head of the instrument comes into abutment with the bottom of the bore (13g) of the catch (13) and drives the catch upward so that the bridge (8b) of the cap engages in the slit (13e) of the catch (FIGS. 8, 9 and FIG. 14). At this stage, the instrument is held in place axially but not locked for rotation because the lever (10) is inscribed inside the groove of the instrument and the spring (14) is compressed under the effect of the translational movement of the catch (13).

Figure 15:
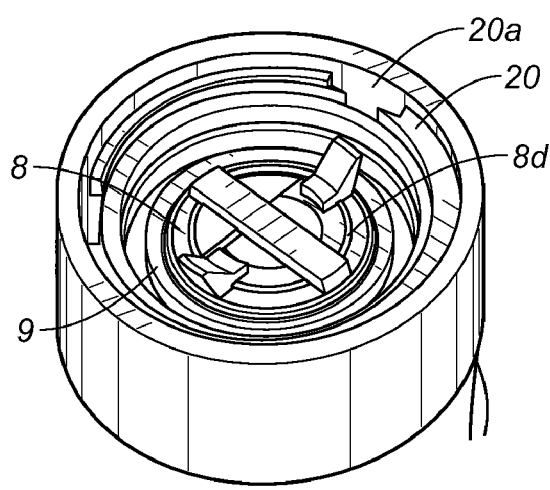

Thereafter, under the effect of a relative rotational movement of the head with respect to the axis (4) of the instrument, the flat (3) of the instrument comes into coincidence with the lateral plane (13d) of the catch (FIGS. 10 and 15), and this has the effect of preventing the instrument from turning.

In the case depicted in FIG. 5, the flat of the instrument is placed directly facing the lateral plane (13d) of the catch, which means that it does not slide upward and the rotational movement is omitted.

The instrument is released by pressing the button (17) which separates the points (12) of the levers and radially retracts the pegs (10a), FIG. 13. The elasticity of the levers allows the pegs to spring back automatically.

It will be noted that, in order to make the figures easier to understand, the push-button return spring has not been depicted.

Alternative forms of embodiment of the invention are conceivable.

In particular, it is possible to propose other shapes of catch, that can be retracted axially, like the one described by way of example, and also catches that can be retracted radially. All these forms of embodiment having the common feature that, on the one hand, retraction occurs if the flat of the instrument is not offered up at the correct angle and, on the other hand, a position is adopted that engages and rotationally drives the instrument as soon as the flat of the instrument is aligned with a corresponding flat belonging to the catch.

The advantages and results of the invention are, in particular, as follows:

The instrument can be inserted and latched into the head of the contra-angle handpiece without the dentist picking up the instrument or coming into contact with it, and this can be done without the correct angular position for the instrument having to be found beforehand.

Insertion and latching are performed using simple and quick movements (the rotation is less than one-quarter of a turn).

Detachment can be performed quickly and simply by operating the push-button.

The latching assembly can be produced in the form of a cartridge or of a sleeve in which the mechanical components of the latch are mounted, this cartridge being mounted without screwing and being held in place by the keying effect with the driving pinion support element fitting into the bore perpendicular to the axis of the instrument (not depicted). This arrangement makes for simple fitting and removal, and makes maintenance easier.

It is possible to produce a wedge that is cylindrical and symmetric with respect to the plane (13d) and which, having been machined along the plane (13d), yields two catches like the one depicted in the figures.

I claim:

1. A head assembly for attaching to a dental instrument in which the dental instrument has a shank formed of a cylindrical body and an annular latching groove, said shank having a drive flat extending parallel to a longitudinal axis of the instrument, the head assembly comprising:
   a rotary shaft having a pinion thereon, said rotary shaft being mounted in an upper bearing and a lower bearing, said rotary shaft having a central bore suitable for receiving the shank of the dental instrument therein;
   a body having said rotary shaft and said upper and lower bearings therein, said body having a circular opening closed off by a push button, said push button being cooperative with said rotary shaft so as to release the shank of the dental instrument therefrom;
   at least one retractable latching lever having a peg extending inwardly therefrom, said peg having a size suitable for fitting into the annular latching groove; and
   a retractable catch connected to said rotary shaft so as to rotate with said rotary shaft, said retractable catch having a positioning plane suitable for coinciding with the drive flat of the dental instrument, said rotary shaft being covered by a cap such that said cap rotates and translates therewith, said cap being positioned in one of said upper bearing and said lower bearing, said retractable catch resting on said pinion and held captive in said cap so as to be slidable therein.

2. The head assembly of claim 1, said retractable catch being longitudinally retractable.

3. The head assembly of claim 1, said retractable catch being radially retractable.

4. The head assembly of claim 1, said cap having a cylindrical envelope mounted coaxial to said longitudinal axis of said rotary shaft, said cap having a bridge secured to said envelope and positioned diametrically on a top of said envelope, said envelope having an external peripheral stop, said retractable catch having a shape defined by a lower plane that rests upon an upper surface of said shaft and an upper plane that can abut an underside of said bridge, said retractable catch having a cylindrical outer envelope having a concavity similar to a concavity on an inside of said cylindrical envelop of said cap, said retractable catch having a lateral plane perpendicular to said upper plane and said lower plane, said retractable catch having a slit positioned radially and transversely at a top thereof, said retractable catch having a longitudinal cylindrical groove extending on a lateral wall thereof for a portion of a length thereof, the head assembly further comprising:
   a compression spring held captive between a bottom of said longitudinal cylindrical groove and an underside of said bridge, said retractable catch having a cylindrical internal bore.

5. The head assembly of claim 4, said cylindrical envelope of said cap having a pair of diametrically opposed slits extending over an entire length thereof, said pair of diametrically-opposed slits being dimensional such that the at least one retractable latching lever can deform and engage with the slits so as to keep the pegs radially apart.

6. The head assembly of claim 5, the at least one retractable latching lever being immobilized at a bottom thereof.

7. The head assembly of claim 1, further comprising:
   a sleeve received within said body, said body having a lower shoulder, said sleeve having an end in abutment with said lower shoulder.

8. The head assembly of claim 7, said sleeve being positioned within said body.

9. The head assembly of claim 1, the at least one retractable latching lever having a bottom end pressing against an upper surface of said pinion, the at least one retractable latching lever having a top end extended by an inclined point diverging therefrom, said top end of the at least one retractable latching lever having an internally inclined plane.

* * * * *